United States Patent
Schröder

[11] Patent Number: 5,938,656
[45] Date of Patent: Aug. 17, 1999

[54] PROCESS AND DEVICE FOR CORRECTING THE SHAPE OF A LENS

[75] Inventor: Eckhard Schröder, Eckental, Germany

[73] Assignee: Aesculap-Meditec GmbH, Jena, Germany

[21] Appl. No.: 08/407,017

[22] PCT Filed: Sep. 23, 1993

[86] PCT No.: PCT/EP93/02577

§ 371 Date: Apr. 28, 1995

§ 102(e) Date: Apr. 28, 1995

[87] PCT Pub. No.: WO94/07422

PCT Pub. Date: Apr. 14, 1994

[30] Foreign Application Priority Data

Sep. 30, 1992 [DE] Germany .............. 42 32 690

[51] Int. Cl.$^6$ .............................. A61N 5/02
[52] U.S. Cl. ................ 606/5; 606/3; 606/10; 606/12; 606/17
[58] Field of Search ............... 606/2, 3–19

[56] References Cited

U.S. PATENT DOCUMENTS

| | | |
|---|---|---|
| 4,665,913 | 5/1987 | L'Esperance, Jr. . |
| 4,729,372 | 3/1988 | L'Esperance, Jr. . |
| 4,941,093 | 7/1990 | Marshall et al. . |
| 5,061,342 | 10/1991 | Jones ............................ 606/5 |
| 5,284,477 | 2/1994 | Hanna et al. ................. 606/5 |

FOREIGN PATENT DOCUMENTS

| | | |
|---|---|---|
| 0 296 982 | 12/1988 | European Pat. Off. . |
| 0 151 869 | 1/1990 | European Pat. Off. . |
| 0 417 952 A2 | 3/1991 | European Pat. Off. . |
| 62-168688 | 7/1987 | Japan . |
| 63-222483 | 9/1988 | Japan . |
| 3-155491 | 7/1991 | Japan . |
| WO 92/00711 | 7/1990 | WIPO . |
| 9200711 | 1/1992 | WIPO ............................. 606/5 |

*Primary Examiner*—David M. Shay
*Attorney, Agent, or Firm*—Barry R. Lipsitz; Ralph F. Hoppin

[57] ABSTRACT

In order to render possible the ablation to different depths in a process for correcting the shape of a lens in which the surface of the lens is acted upon by the radiation of a pulsed radiation source through a shutter in specific regions exposed by the shutter and thereby removing material from the lens by the radiation effect during the impingement of each radiation pulse, wherein the radiation is concentrated in a bundle of rays, the cross section of which is smaller when striking the lens surface than that of the lens surface exposed by the shutter, and wherein the bundle of rays is moved such that the entire lens surface exposed by the shutter is irradiated by radiation pulses consecutively impinging on the lens surface, it is suggested that the bundle of rays is moved between successive radiation pulses only to such an extent that the regions of the lens surface struck by the radiation pulses consecutively impinging on the lens surface partially overlap. A device is also suggested for performing this process.

16 Claims, 2 Drawing Sheets

PROCESS AND DEVICE FOR CORRECTING THE SHAPE OF A LENS

The invention relates to a process for correcting the shape of a lens, in which the surface of the lens is acted upon by the radiation of a pulsed radiation source through a shutter in specific regions exposed by the shutter and thereby removing material from the lens by the radiation effect during the impingement of each radiation pulse, wherein the radiation is concentrated in a bundle of rays, the cross section of which is smaller when striking the lens surface than that of the lens surface exposed by the shutter, and wherein the bundle of rays is moved such that the entire lens surface exposed by the shutter is irradiated by radiation pulses consecutively impinging on the lens surface.

Furthermore, the invention relates to a device for performing this process.

With the described process, it is possible to form the shape of the surface of a lens, for example a contact lens or also the cornea of the eye by so-called photo-ablation, such that an optical correction of the surface can be achieved. Usually lasers are used for this purpose as radiation sources, namely pulsed lasers which repeatedly emit radiation pulses in timed succession. These radiation pulses are directed onto the lens surface via shutters corresponding with the desired correction and remove a very small amount of material from the lens surface at each impingement.

It is known in processes of this type to have the entire area of the lens surface exposed by the shutter completely irradiated by each radiation pulse, i.e. the cross section of the bundle of rays directed onto the shutter is then larger at each radiation pulse than that of the area exposed by the shutter. In this respect, problems concerning intensity can result, since the entire radiation generated by the laser must possibly be distributed over a relatively large area.

On the other hand, it is known to concentrate the radiation energy generated by the laser in a bundle of rays having a very small cross section, wherein this bundle of rays scans the lens surface exposed by the shutter in a manner similar to a scanner. In this respect, it is very difficult to achieve a uniform irradiation of the entire area, since the positions of the radiation pulse have to adjoin each other exactly.

In a further known process, the radiation is concentrated in a beam-shaped area which is guided stepwise over the area exposed by the shutter. In this respect, only a portion of the exposed area is irradiated at each irradiation, the connection of these portions to each other, however, is easier to accomplish.

In all the described processes, the area exposed by the shutter is ultimately struck at every point by a radiation pulse, thus, a more or less uniform ablation results in the entire region exposed by the shutter, the depth of this ablation corresponding with the ablation of one radiation pulse.

When a greater ablation is desired, it is normally necessary to repeat the procedure as a whole.

The object of the invention is to perform a process of the type described at the outset such that already during a first irradiation procedure, an ablation depth can also be attained which corresponds with multiple irradiation.

This object is accomplished in accordance with the invention in a process of the type described in the beginning, in that the bundle of rays is moved between successive radiation pulses only to such an extent that the regions of the lens surface struck by the radiation pulses consecutively impinging on the lens surface partially overlap. Depending on the extent of the overlapping, radiation pulses repeatedly impinge on the lens surface to be shaped in the overlapping region so that a greater ablation depth can also be achieved. For example, two radiation pulses strike in each region with an overlap of adjacent radiation cross sections of 50%, three radiation pulses with an overlap of 67%, etc. Thereby, it is possible to achieve an ablation to the desired depth in one procedure.

In principle, such a process can be performed with every form of cross section of the bundle of rays which makes a completely uniform irradiation of the area exposed by the shutter possible during scanning, however, it is particularly advantageous when the cross section of the bundle of rays has the shape of a rectangular beam which completely covers the area exposed by the shutter in one direction, however in the direction extending vertically thereto only to a small extent, and when the beam is moved between consecutive radiation pulses in this direction extending vertically. The beams consecutively striking the lens surface overlap once or several times when crossing the area exposed by the shutter, so that a very uniform irradiation of the lens surface can be achieved with an exactly defined number of impinging radiation pulses. It is important when using a beam-shaped radiation cross section that the lens surface can be irradiated with a relatively high power density, which is also sufficient in relatively small lasers to achieve the desired removal of material.

The shutter is only moved into a new position when the entire area of the lens surface exposed by this shutter has been struck by radiation pulses.

In this respect, it is advantageous when the shutter is rotated stepwise about the optical axis of the lens.

Thereby, the extent of the overlapping of the regions of the lens surface struck by radiation pulses consecutively impinging on the lens surface is varied when sweeping over a shutter opening. The lens surface exposed by the shutter opening is thus ablated to different depths, so that the degree of ablation can be controlled by the overlapping.

In another embodiment in which the shutter is rotated stepwise about the optical axis of the lens, a shutter opening can be used which is not rotationally symmetrical with respect to the axis of rotation of the shutter, and the extent of the overlapping of the regions of the lens surface struck by radiation pulses consecutively impinging on the lens surface is selected to vary at different positions of the shutter. At each individual position of the shutter opening, the overlapping thus remains constant, so that material is removed to the same depth from the entire region of the lens surface exposed by the shutter in one shutter position. As opposed to this, by varying the overlapping at different angular positions of the shutter, an ablation can be achieved which is different in different angular regions so that, for example, it is possible to correct myopia or hyperopia, namely in addition to the different depths of ablation in radial direction which result due to the form of the shutter.

The object of the invention is also to create a device for performing the described process. Such a device is described in patent claim 7. Advantageous developments result from patent claims 8 to 12.

The following description of a preferred embodiment of the invention serves to explain the invention in greater detail in conjunction with the drawings. In the drawings.

Figure 1:
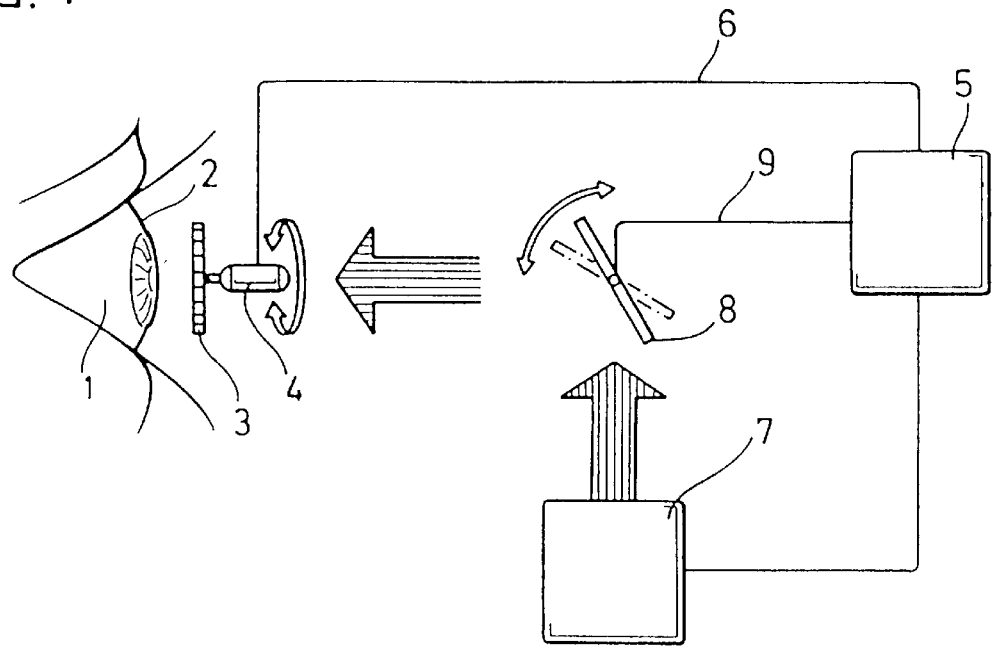
FIG. 1 is a schematic view of a device for correcting the shape of a lens.

The invention is explained in the following using the shaping of the cornea of an eye 1 as an example, however, it is to be understood that also other lenses can be shaped in this manner, for example, contact lenses.

A shutter 3 is arranged in front of the cornea generally described in the following as lens 2, this shutter being rotatable stepwise about the optical axis of the lens 2 and having a gap which exposes a portion of the surface of the lens 2, whereby the free portion of the lens 2 changes from position to position of the shutter 3. The shutter 3 is rotated stepwise by a stepping motor 4, the motor 4 is controlled by a control 5 via a line 6.

This control 5 also controls a laser 7, for example an excimer laser with a wavelength of 193 nm, which emits radiation pulses when controlled by the control 5. These radiation pulses are directed via a deflecting mirror 8 onto the shutter 3 and through its free portions onto the surface of the lens 2.

The deflecting mirror 8 is provided with a drive which is actuated by the control 5 via a further line 9. Thereby, the pivoting angle of the deflecting mirror 8 can be changed, in FIG. 1 two different pivoting angles are represented by solid or dot-dash lines, whereby the differences in the angle of deviation are enlarged excessively in the drawing for better illustration.

Optical means are not represented in the drawing, for example cylinder lenses, which shape the cross section of the rays of the radiation emitted by the laser 7 such that the cross section of the rays has the shape of a flat elongated rectangle or beam.

This beam has measurements which are greater in one direction than the opening in the shutter 3, however, considerably smaller in the direction lying vertical thereto, so that at each radiation pulse only a beam-shaped region of the surface of the lens 2 exposed by the shutter 3 is struck by the radiation.

Figure 2:
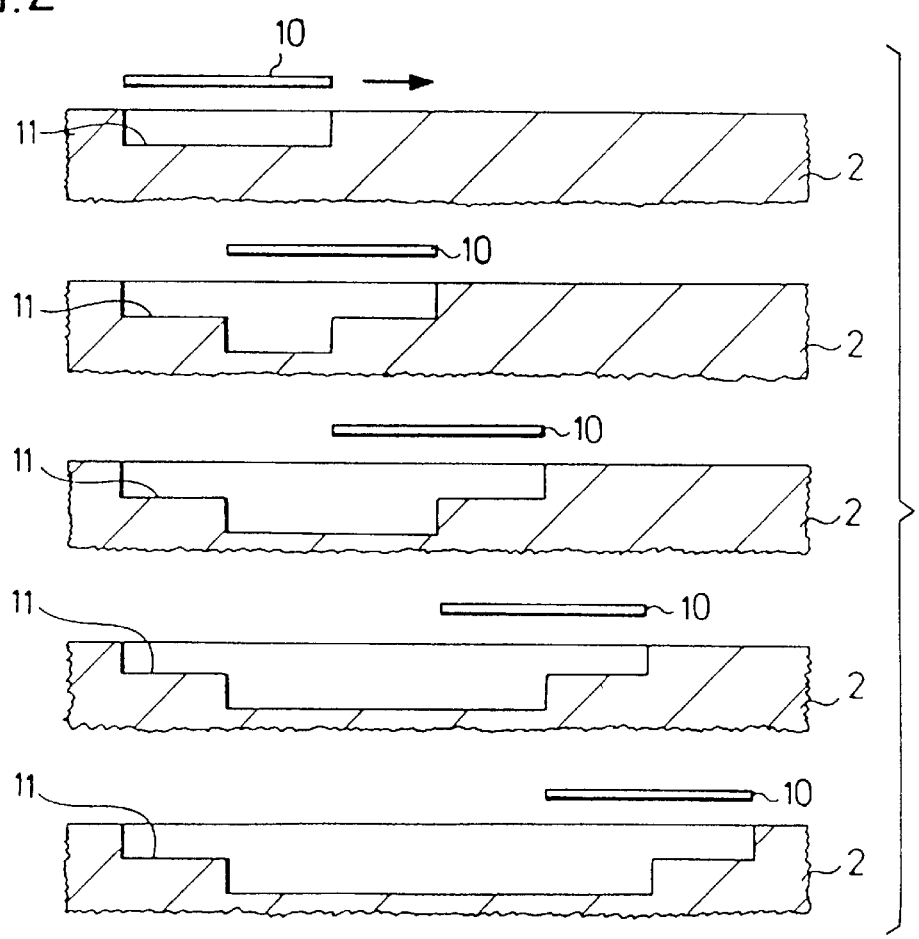
FIG. 2 is a schematic cross-sectional view of the irradiated lens in five successive irradiation steps with a step width which corresponds with half of the cross section of the radiation.

The effect of this radiation pulse with beam-shaped cross section impinging on the surface of the lens 2 is schematically represented in FIG. 2. In this respect, the area of the beam taken up by the radiation pulse is indicated by an elongated rectangle 10 above the surface of the lens 2, whereby this rectangle only extends in the drawing plane over a portion of the lens surface which is exposed by the shutter, while vertical to the drawing plane an essentially greater extension is provided which covers the entire opening exposed by the shutter. Therefore, the rectangle 10 merely symbolizes the expansion of the cross section of the impinging radiation pulses in the direction of deflection of the radiation cross section.

In the topmost representation of FIG. 2, it is shown how a recess 11 is "burnt" into the lens surface when a radiation pulse strikes, the expansion of this recess essentially corresponding with the expansion of the radiation cross section (symbolized by the rectangle 10). The depth of the recess 11 results from the energy which is applied by a radiation pulse to the irradiated area.

In accordance with the invention, the radiation cross section is displaced relative to the lens 2 after every radiation pulse by swivelling the deflecting mirror 8, namely only to the extent that a partial covering or overlapping remains. In the case of FIG. 2, the path of displacement of the radiation cross section consists of half of the width of the beam-shaped irradiation region, in FIG. 2 this becomes clear in that the rectangle 10 is displaced by half of its length.

When a radiation pulse strikes the lens surface again in this position, then material is removed again in the irradiation region to a depth which corresponds with the depth of the recess 11. Due to the 50% overlapping, a depth results in the central region over a length of half of the radiation cross section, this depth corresponding with twice the depth of the recess 11, as is represented in the second stage in FIG. 2.

In the three following stages of FIG. 2, the radiation cross section is displaced further by half a rectangle width each time. It is apparent that in this manner, the surface of the lens 2 is ablated to such a depth as would correspond with the energy of two impinging radiation pulses, merely in the peripheral region a graduation results. In this manner, an ablation is attained which has twice the depth of a normal ablation during which the area exposed by the shutter is struck once in total by radiation pulses.

Figure 3:
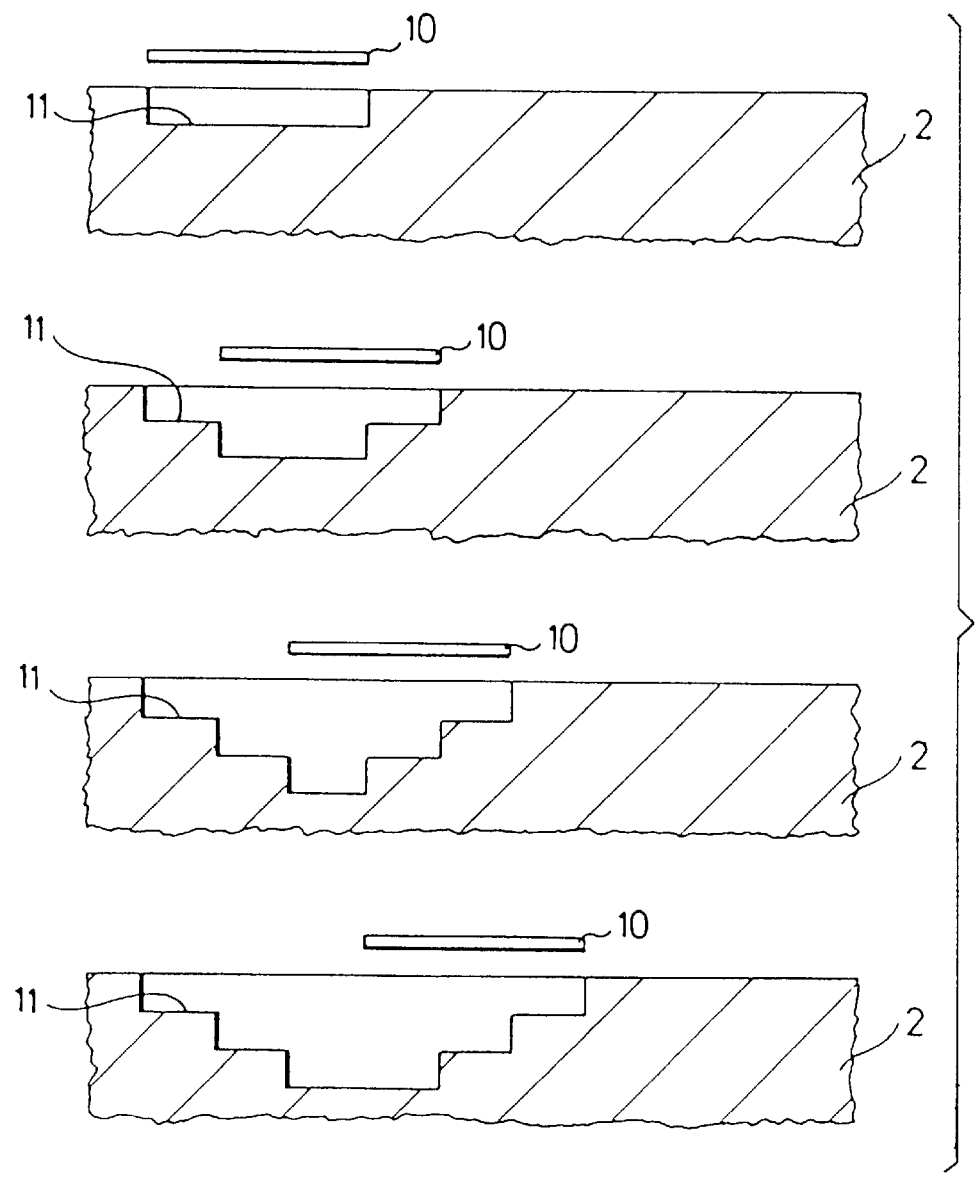
FIG. 3 is a view similar to FIG. 2 with four successive irradiation steps, wherein the step width only amounts to a third of the cross section of the radiation.

In FIG. 3, the corresponding procedure for a displacement of the radiation cross section over a shorter path of displacement is described, namely a displacement over a third of the width of the rectangle 10. It can be seen that an ablation can be achieved in this manner, which corresponds with triple the ablation amount during single irradiation. Also in this respect, a graduation in the peripheral region results.

This control naturally results in the possibility not to keep the overlapping in the region exposed by the shutter constant over its entire region but to vary it, so that in this manner a varying profiling can be achieved in the direction of displacement of the radiation cross section. For this purpose, it is sufficient to vary the step width of the pivoting movement of the deflecting mirror 8 via the control 5.

With the control it is also possible to undertake spherical corrections of the lens surface, namely simultaneously with aspherical corrections, as for example astigmatism. This can be achieved in that the shutter is rotated stepwise and that at each shutter position the overlapping is selected by the control to vary so that, as a whole, a different ablation rate occurs for different angular positions of the shutter. This leads to a spherical correction while at the same time the shutter form is responsible for the aspherical correction.

I claim:

1. A device for correcting the shape of a lens area, comprising:

a pulsed radiation source, a control, a controllable optical means, and a shutter, wherein:

radiation in the form of radiation pulses from said pulsed radiation source is adapted to act on a surface of the lens in specific regions via an opening in said shutter exposing only a portion of said area, thereby removing material from the lens during an impingement of each radiation pulse, said radiation is concentrated in a bundle of rays having a cross section when striking the lens surface that is smaller than the lens surface exposed by the shutter, said controllable optical means move said bundle of rays in a stepwise manner within said opening such that the entire lens surface exposed by the shutter is irradiated in successive steps by partially overlapping radiation pulses consecutively impinging on the lens surface to enable the lens surface exposed by the shutter opening to be ablated to different depths, and wherein said control varies a step width of a stepwise movement of said controllable optical means when the position of said shutter is fixed.

2. A device according to claim 1, wherein the control rotates the shutter stepwise about an optical axis of the lens.

3. A device according to claim 1, wherein the control moves the shutter into a new position only when the entire lens surface exposed by the shutter has been struck by radiation pulses.

4. A device according to claim 3, wherein the control rotates the shutter stepwise about an optical axis of the lens.

5. A device according to claim 1, wherein:
- the cross section of the bundle of rays has the shape of a rectangular beam covering the entire lens surface exposed by the shutter completely in one direction, but only to a small extent in a direction extending transversely thereto, and
- the controllable optical means move the beam in said transversely extending direction between consecutive radiation pulses.

6. A device according to claim 5, wherein the control rotates the shutter stepwise about an optical axis of the lens.

7. A device according to claim 5, wherein the control moves the shutter into a new position only when the entire lens surface exposed by the shutter has been struck by radiation pulses.

8. A device according to claim 7, wherein the control rotates the shutter stepwise about an optical axis of the lens.

9. A device for correcting the shape of a lens area, comprising:
- a pulsed radiation source,
- a control,
- a controllable optical means, and
- a shutter, wherein:
  - radiation in the form of radiation pulses from said pulsed radiation source is adapted to act on a surface of the lens in specific regions via an opening in said shutter exposing only a portion of said area, thereby removing material from the lens during an impingement of each radiation pulse,
  - said radiation is concentrated in a bundle of rays having a cross section when striking the lens surface that is smaller than the lens surface exposed by the shutter,
  - said controllable optical means move said bundle of rays in a stepwise manner within said opening such that the entire lens surface exposed by the shutter is irradiated in successive steps by partially overlapping radiation pulses consecutively impinging on the lens surface to enable the lens surface exposed by the shutter opening to be ablated to different depths, and
  - wherein said control varies a step width of a stepwise movement of said controllable optical means between different positions of said shutter.

10. A device according to claim 9, wherein the control rotates the shutter stepwise about an optical axis of the lens.

11. A device according to claim 9, wherein the control moves the shutter into a new position only when the entire lens surface exposed by the shutter has been struck by radiation pulses.

12. A device according to claim 1, wherein the control rotates the shutter stepwise about an optical axis of the lens.

13. A device according to claim 9, wherein:
- the cross section of the bundle of rays has the shape of a rectangular beam covering the entire lens surface exposed by the shutter completely in one direction, but only to a small extent in a direction extending transversely thereto, and
- the controllable optical means move the beam in said transversely extending direction between consecutive radiation pulses.

14. A device according to claim 13, wherein the control rotates the shutter stepwise about an optical axis of the lens.

15. A device according to claim 13, wherein the control moves the shutter into a new position only when the entire lens surface exposed by the shutter has been struck by radiation pulses.

16. A device according to claim 15, wherein the control rotates the shutter stepwise about an optical axis of the lens.

* * * * *